United States Patent [19]

Van der Knaap

[11] Patent Number: Plant 6,738

[45] Date of Patent: Apr. 18, 1989

[54] CHRYSANTHEMUM PLANT NAMED BYRON

[75] Inventor: Jacques C. M. Van der Knaap, De Lier, Netherlands

[73] Assignee: Fides Beheer B.V., De Lier, Netherlands

[21] Appl. No.: 123,905

[22] Filed: Nov. 23, 1987

[51] Int. Cl.[4] ..... A01H 5/00

[52] U.S. Cl. ..... Plt./74

[58] Field of Search ..... Plt. 74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Byron, having generally flat capitulum form and bronze-yellow ray florets. Although the capitulum type is single, the quantity and positioning of the ray florets gives the new cultivar almost the appearance of being double. The individual ray florets are also unusually wide, being 1.5 cm in width or even larger.

1 Drawing Sheet

The present invention comprises a new and distinct cultivar of *Chrysanthemum morifolium,* hereinafter referred to by the cultivar name Byron.

Byron is a product of a planned breeding program which had the objective of creating new Chrysanthemum cultivars with single capitulum type, bronze-yellow ray florets, nine (9) week response, and the ability to produce commercially acceptable quality in year around cut mum programs. Such traits in combination were not present or needed improvement in previously available commercial cultivars.

Byron was originated from a hybridization made by applicant in a controlled breeding program in De Lier, Holland in 1983. The female parent was Quick, an unpatented and non-commercial cultivar. The male parent of Byron was Fleur, an unpatented cultivar commercially available in Europe.

Byron was discovered and selected as one flowering plant within the progeny of the stated parentage by Jacques C. M. Van der Knaap in July 1983 in a controlled environment in De Lier, Holland.

The first act of asexual reproduction of Byron was accomplished when vegetative cuttings were taken from the initial selection in September 1983 in a controlled environment in De Lier, Holland by a technician working under formulations established and supervised by Jacques C. M. Van der Knapp. Horticultural examination of selected units initiated in March 1984 has demonstrated that the combination of characteristics as herein disclosed for Byron are firmly fixed and are retained through successive generations of asexual reproduction.

Byron has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Byron, which in combination distinguish this Chrysanthemum as a new and distinct cultivar:

1. Flat capitulum form.

2. Capitulum type is single but the quantity and placement of petals gives Byron almost the appearance of being double.

3. Bronze-yellow ray florets.

4. Individual ray florets are wide relative to their length.

5. Diameter across the face of the capitulum is 55–65 mm.

6. Green (immature) to yellow (mature) disc florets.

Of the many commercial cultivars known to the present inventor, the most similar in comparison to Byron is Dramatic, disclosed in U.S. Plant Pat. No. 3,189. In comparison to Dramatic, Byron has better vigor, later response, less compounding, better leaves, and a distinct bronze tone in the ray florets. The capitulum form, capitulum type, and disc floret color are similar to those same characteristics of Dramatic.

The accompanying photographic drawing shows in top perspective view typical inflorescence and foliage characteristics of Byron, with colors being as nearly true as possible with illustrations of this type.

In the following description, color references are made to The Royal Horticultural Society Colour Chart. The color values were determined between 11:00–12:00 a.m. in October 1985 under natural daylight at De Lier, Holland.

Classification:

*Botanical.*—*Chrysanthemum morifolium,* Ramat., cv. Byron.

*Commercial.*—Cut daisy spray.

INFLORESCENCE

A. Capitulum:

*Form.*—Flat.

*Type.*—Daisy.

*Diameter across face.*—55–65 mm.

B. Corolla of ray florets:

*Color (general tonality from a distance of three meters).*—Bronze-yellow.

*Color (upper surface).*—12A.

*Size.*—The width of the individual petals is unusually large, being 1.5 cm or even greater.

C. Corolla of disc florets:

*Color (mature).*—Yellow.

*Color (immature).*—Green.

D. Reproductive organs:

*Androecium.*—Present only in disc florets; numerous.

*Gynoecium.*—Present in both ray and disc florets; numerous.

PLANT

A. General appearance:

*Height.*—80 cm.

B. Foliage:

*Color* (*upper surface*).—146A.

*Color* (*under surface*).—146B.

*Shape.*—Pinnately lobed.

I claim:

1. A new and distinct cultivar of Chrysanthemum plant named Byron, as described and illustrated, and parts thereof.

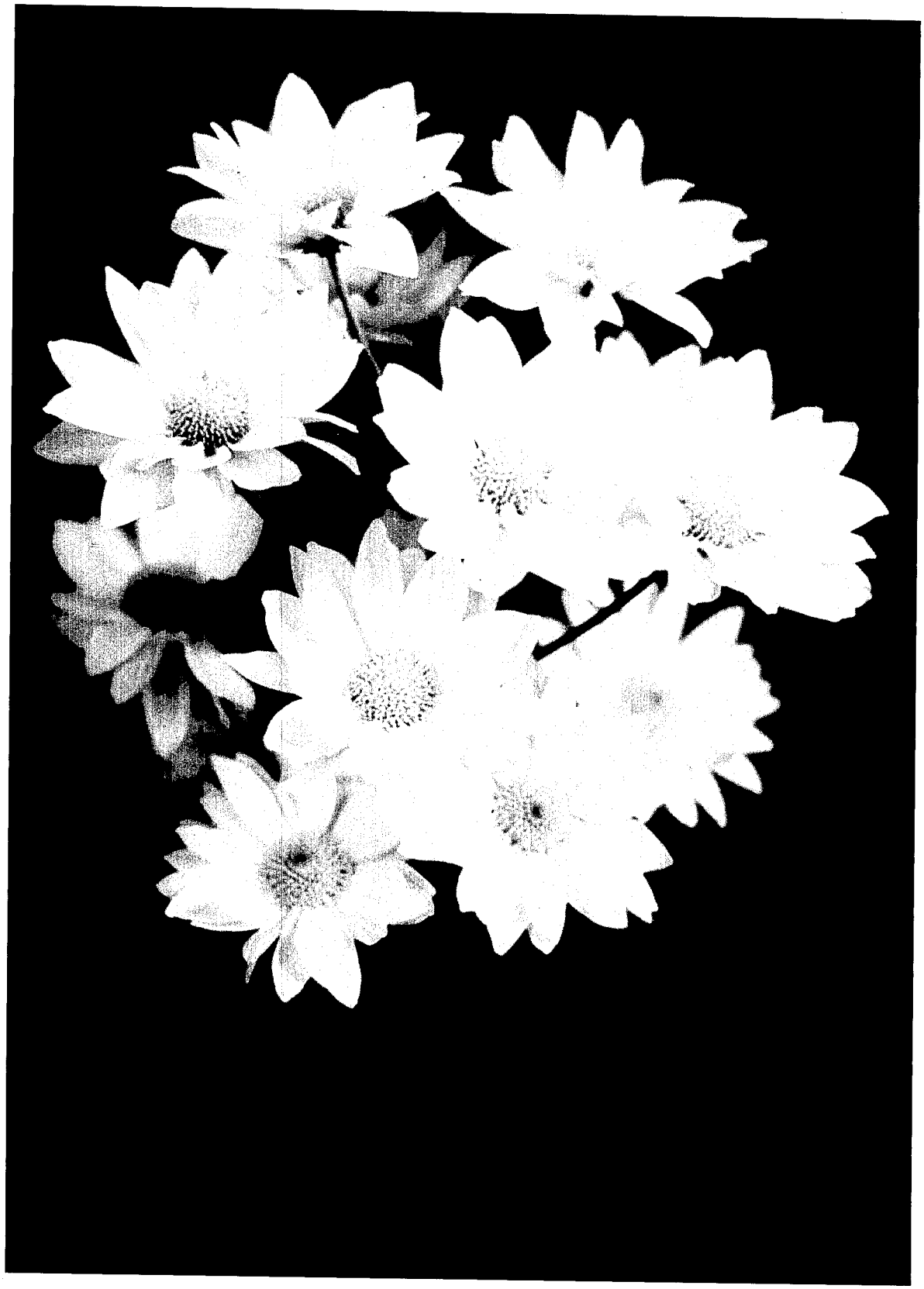

* * * * *